United States Patent [19]

Elmovist

[11] 4,318,411
[45] Mar. 9, 1982

[54] HEART PACEMAKER

[75] Inventor: Hakan Elmovist, Bromma, Sweden

[73] Assignee: Siemens Aktiengesellschaft, Berlin & Munich, Fed. Rep. of Germany

[21] Appl. No.: 185,546

[22] Filed: Sep. 9, 1980

[30] Foreign Application Priority Data

Sep. 27, 1979 [DE] Fed. Rep. of Germany ....... 2939254

[51] Int. Cl.$^3$ ............................................. A61N 1/36
[52] U.S. Cl. ........................ 128/419 PG; 128/419 PT
[58] Field of Search .................... 128/419 PG, 419 PT

[56] References Cited

U.S. PATENT DOCUMENTS

| | | | |
|---|---|---|---|
| 3,557,796 | 1/1971 | Keller et al. ................. | 128/419 PG |
| 3,939,844 | 2/1976 | Pequignot .................... | 128/419 PG |
| 4,120,307 | 10/1978 | Jirak et al. .................... | 128/419 PT |
| 4,192,316 | 3/1980 | Walters et al. ................ | 128/419 PG |

FOREIGN PATENT DOCUMENTS 2006076  2/1970  Fed. Rep. of Germany .

OTHER PUBLICATIONS

"COS/MOS Integrated Circuits", *Data Book RCA*, (1978), title page, Table of Contents, pp. 2 and 242.

*Primary Examiner*—William E. Kamm

*Attorney, Agent, or Firm*—Hill, Van Santen, Steadman, Chiara & Simpson

[57] ABSTRACT

The exemplary embodiment comprises a pulse generator which is controlled by means of a parent frequency generator with a prescribable parent frequency, and a control circuit with setting generator for setting desired pulse repetition rates of the pulse generator for the heart pacemaker pulses as a function of the setting value of the setting generator. The purpose of the disclosure is to develop such a heart pacemaker with simple technical means to such end that a preselection of the pulse repetition rate of the heart pacemaker is possible directly in pulse per minute. This goal is inventively achieved in that the parent frequency signal ($f_o$) of the parent frequency generator is supplied to a binary frequency multiplier together with a binary multiplication signal (n) of a multiplication signal generator which is adjustable as a function of a pulse per minute setting value (F) of a pulse per minute setting generator, said binary frequency multiplier converting the parent frequency ($f_o$) of the parent frequency signal into a secondary frequency ($f_1$) which is composed of a fraction ($f_o/(n_{max}+1)$) of a parent frequency predetermined by the multiplier, multiplied by the binary value (n) of the multiplication signal.

6 Claims, 2 Drawing Figures

HEART PACEMAKER

BACKGROUND OF THE INVENTION

The invention relates to a heart pacemaker with a pulse generator which is controlled by means of a parent frequency generator with a prescribable parent frequency, and with a control circuit with a setting generator for setting the desired pulse repetition rates of the pulse generator for the heart pacemaker pulses as a function of the setting value of the setting generator.

A heart pacemaker of this type is known, for example, from the German OS No. 2,006,076. A feature of this heart pacemaker, however, is that the preselection of desired pulse repetition rates is only possible by means of setting the time interval value between two successive pulses in milliseconds. A setting in terms of pulse intervals, however, is a type of heart rate preselection which is not generally standard. The heart rate is the more usual measure for judging the heat activity of a patient, not only for the general public but, rather, also for the expert, i.e. the physician in the specific case. In general, one can immediately determine from the specification of a heart rate value whether or not a critical state of heart activity exists for the patient. Accordingly, even in the case of heart pacemaker patients, the heart pacemaker can only be optimally adapted to the patient's requirements in terms of its output frequency when the frequency to which the heart pacemaker is to be set can be adjusted in advance in pulses per minute.

SUMMARY OF THE INVENTION

Given a heart pacemaker of the type initially cited, the object of the present invention is to provide such a setting of pulses per minute, whereby, however, the overall technical outlay is to be kept to an optimum minimum.

This object is inventively achieved in that the present frequency signal of the primary frequency generator is conducted to a binary frequency multiplier together with a binary multiplication signal of a multiplication signal generator which can be set as a function of a pulse per minute setting value of a pulse per minute setting generator, said binary frequency multiplier converting the parent frequency of the parent frequency signal to a secondary frequency which is composed of a fraction of the parent frequency prescribed by means of the multiplier, multiplied by the binary value of the multiplication signal.

In the simplest manner, thus, the invention allows for the adjustment as a function of a pulse per minute setting value. The technical outlay required for achieving this result is at an optimum minimum. Binary frequency multipliers as are employed, among other things, in order to achieve the inventive result, are commercially available and are described, for example, in the data book RCA Solid State "COS/MOS Integrated Circuits", dating from the year 1978, and specifically for four bit execution on page 242.

Further advantageous developments of the invention proceed from the subclaims.

In the following, an exemplary embodiment of the invention is described in greater detail on the basis of two Figures on the accompanying drawing sheet; and other objects, features, and advantages will be apparent from this detailed disclosure and from the appended claims.

DETAILED DESCRIPTION

Figure 1:
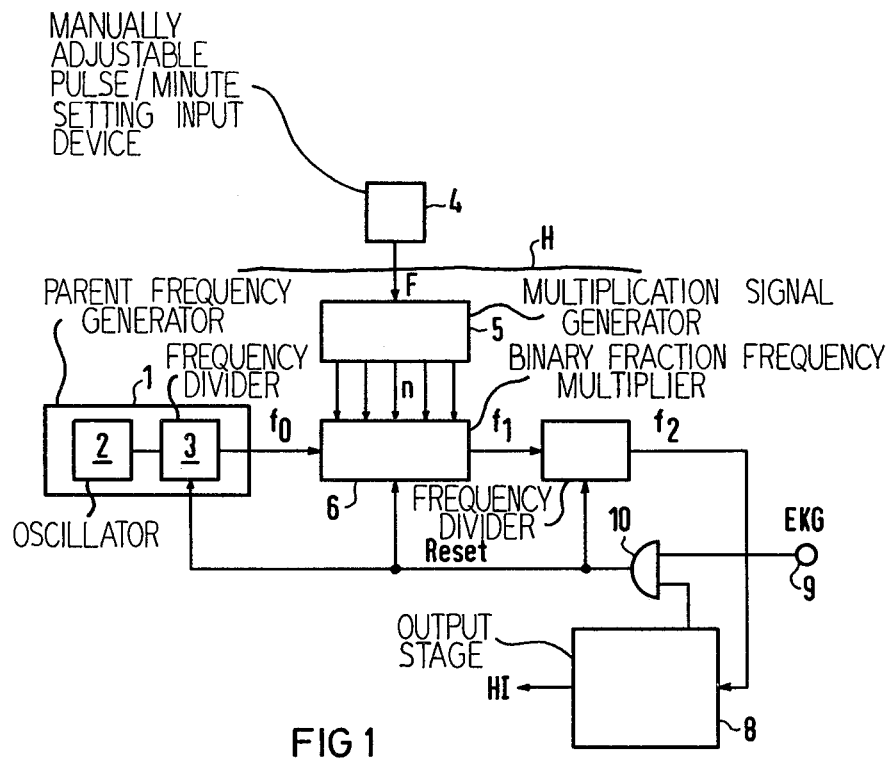
FIG. 1 is a circuit diagram illustrating an embodiment of the invention.

Under the reference 1, FIG. 1 shows a parent frequency generator which generates output pulses of the pulse repetition rate $f_0$. For example, in the present case, the frequency $f_0$ should amount to 333.3 hertz. The parent frequency generator 1 comprises, for example, a frequency oscillator 2 which oscillates at a specific frequency which is reduced to the desired frequency $f_0$ by means of a subsequent frequency divider 3, for example, a counter. Together with a binary-coded whole-number multiplication signal, representing a decimal value n, supplied by a multiplication signal generator 5 which is adjustable as a function of a pulse per minute setting value F of a manually adjustable pulse per minute setting input device or generator 4, the said parent frequency $f_0$ is supplied to a binary frequency multiplier 6. The binary frequency multiplier converts the parent frequency $f_0$ into a secondary frequency $f_1$ which is equal to a fraction $f_0/(n_{max}+1)$ of the parent frequency prescribed by the multiplier, multiplied by the decimal value n of the binary coded multiplication signal. In the present case, thus, proceeding from a frequency $f_0=333.3$ Hz, the frequency $f_1$ amounts to $f_1=n$ (decimal)$\times 10.42$ Hz upon employment of a five bit binary frequency multiplier with $n_{max}=31$ (decimal) i.e. $n_{max}+1=32$ (decimal).

The output frequency $n \times 10.42$ Hz, however, is still too large by approximately a factor of one hundred for the specification of a stimulation pulse repetition rate in the heart rate range. For this reason, specifically in the present sample embodiment, a frequency divider 7 (counter) follows the binary frequency multiplier 6, said frequency divider 7 dividing the still too high output frequency $f_1$ of the binary frequency multiplier 6 by the factor one hundred and twenty-five (125). The result is an output frequency of the frequency divider 7 of $f_2=n\times 5$ pulses per minute. With the exemplary embodiment, thus there follows the setting possibility in five pulse per minute steps given $n=0$ through $n=n_{max}=31$ (decimal) in the range $f_2=0$ through 155 pulses per minute. However, only the range from approximately 30 through 150 pulses per minute is of interest for the use case with a patient. This range can then be achieved by setting values between $n=6$ (decimal) through 30 (decimal).

In the present exemplary embodiment, the frequencies and components employed have only exemplary character. Of course, one could always make do without additional frequency divider elements if very small parent frequencies $f_o$ are employed from the very outset. These frequencies, however, would then have to lie in the range three hertz (3 Hz) and below. This, however, under certain conditions, leads to undesired regularities in the output frequency of the binary frequency multiplier. Further possibilities of variation derive in that binary frequency multipliers 6 are employed with higher processing bit numbers than, for example, five bits. With an increasing bit number, $n_{max}$ increases accordingly and, thus, so does the division factor for the parent frequency $f_0$. If, in the present case, upon employment of a five bit binary frequency multiplier, the factor $n_{max}$ still amounts to 31 (decimal), then, for example, it already amounts to 255 (decimal) in case a eight bit binary frequency multiplier is employed. In cooperation with an appropriately selected parent input frequency $f_0$, there thus likewise derive other division values for the output frequency. In the exemplary embodiment of FIG. 1, further, a frequency setting in five pulse per minute steps is provided. Of course, smaller partial step values, for example in the range one pulse per minute or two pulses per minute or other intermediate values can also be preselected by means of corresponding modifications.

According to the illustration of FIG. 1, the frequency $f_2 = n \times 5$ pulse per minute is supplied to an output stage 8 in the exemplary embodiment, said output stage 8 being represented in the present case by the pulse generator for the heart pacemaker pulses. The heart pacemaker pulses are referenced with HI; via the illustrated output of the pulse generator 8, they are forwarded in the direction of the arrow via an electrode connection to the heart of the pacemaker patient. Further, the exemplary embodiment of FIG. 1 shows an inhibited pacemaker. This, therefore, exhibits an input 9 at which spontaneous heart reactions are detected by means of monitoring the EKG of the patient (for example by means of tapping via the heart pacemaker electrode as well) and are forwarded to the one input of an AND element 10. The second input of the AND element lies at a pulse generator of output stage 8 for generating the heart pacemaker pulses. If, accordingly, a spontaneous heart pulse occurs at input 9, then a reset pulse for the network consisting of parent frequency generator 1, binary frequency multiplier 6 and frequency divider 7 is forwarded via the AND element 10, so that the controlled elements of this network are set to the initial state by means of said reset pulse. This occurs as often as further spontaneous heart actions are registered via the input 9.

In the exemplary embodiment of FIG. 1, the pulse per minute generator 4 is a device which is separate from the actual pacemaker. In the present case, thus, it is not implanted together with the pacemaker. On the contrary, the pulse per minute generator 4 is designed in such manner that it transmits the setting signals to the implanted multiplication signal generator 5 transcutaneously, i.e. through the surface of the skin H. The multiplication signal generator 5 is designed as a program memory for storing respective data F transmitted by the pulse per minute generator 4. Data once given, accordingly, are retained by the pulse per minute generator 5 until they are replaced by the input of new data from the outside.

Figure 2:
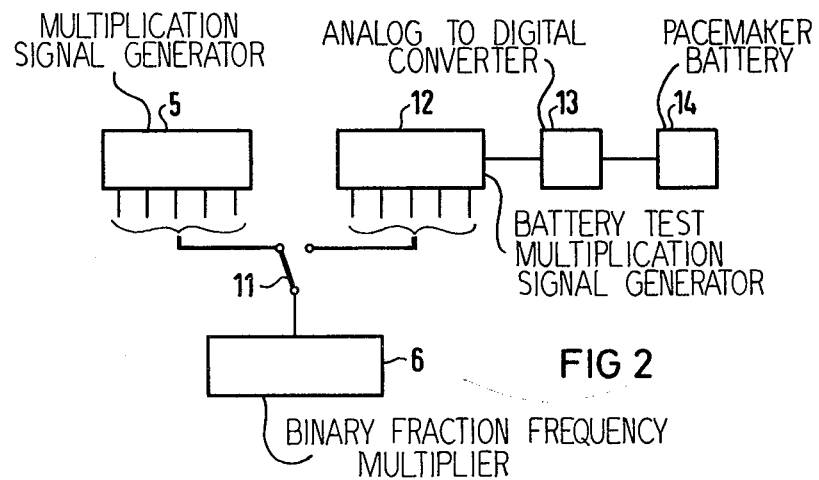
FIG. 2 shows a modification of the embodiment of FIG. 1.

A further modification of the exemplary embodiment of FIG. 1 is illustrated in FIG. 2. The change consists therein that, in this arrangement, a changeover 11 is allocated to the multiplication signal generator 5 at its output lines to allow the binary frequency multiplier 6 to be switched at its input side from control by the binary coded output signal of the multiplication signal generator 5 to control by a corresponding binary coded output of a test frequency generator 12, 13 for the emission of a test frequency for testing, in particular, the state of the battery 14 of the heart pacemaker. In the circuit diagram, the test frequency generator comprises a second multiplication signal generator 12 for the emission of such binary values n for the binary frequency multiplier 6 as are correspondingly adapted to the test frequency. The component 13 is an analog/digital converter for controlling the test frequency supplied by multiplier 6 in the battery-test position of switch 11.

Given the simplest technical structure, thus, the invention explained on the basis of the exemplary embodiment renders possible the preselection of the heart pacemaker frequency by means of direct setting in pulses per minute. In contrast to the prior art, where a presetting of the heart pacemaker pulses is only possible in milliseconds (ms) in accord with the repetition interval T, there thus derives a setting possibility which is better adapted than previously to standard practice. For this reason, an adjustment can now ensue with far greater simplicity and certainty.

It will be apparent that many modifications and variations will be effected without departing from the scope of the novel concepts and teachings of the present invention.

I claim as my invention:

1. A heart pacemaker comprising a controllable pulse generator for generating the heart pacemaker pulses, a parent frequency generator with prescribable parent frequency, and a control circuit including a setting generator for setting desired pulse repetition rates of the pulse generator for the heart pacemaker pulses as a function of the setting value of the setting generator, said setting generator comprising a binary frequency multiplier (6), a multiplication signal generator (5), and a pulse per minute adjustable setting input device (4), the parent frequency signal ($f_0$) of the parent frequency generator (1) being supplied to the binary frequency multiplier (6) together with a binary multiplication signal (n) of the multiplication signal generator (5), and the pulse per minute setting input device (4) controlling the binary multiplication signal (n) to adjust the same as a function of a pulse per minute setting value (F) of the pulse per minute setting input device (4), said binary frequency multiplier (6) converting the parent frequency ($f_0$) of the parent frequency signal into a secondary frequency ($f_1$) which is composed of a fraction ($f_0/(n_{max}+1)$) of the primary frequency prescribed by the multiplier multiplied by the binary value (n) of the multiplication signal.

2. A heart pacemaker according to claim 1, characterized in that the binary frequency multiplier (6) comprises a program memory (5) which can be coupled signal-wise to the pulse per minute setting input device (4), the pulse per minute setting input device being manually adjustable in prescribable pulse per minute steps, for example, in one or five or ten pulse per minute steps, and, as a function of the step number set, the whole-number binary multiplication signal (n) belonging to the adjusted step is automatically set at the program memory.

3. A heart pacemaker according to claim 1, characterized in that frequency dividers (for example 7) are allocated, for example, pre-and/or post-connected to the binary frequency multiplier (6) for further interval subdivision of pulse per minute steps as needed.

4. A heart pacemaker according to claim 1, characterized in that only the program memory (5) is a component of the pacemaker to be implanted; and in that the pulse per minute setting input device (4) is designed for transcutaneous transmissions of its setting signals to the program memory.

5. A heart pacemaker according to claim 1, characterized in that, given design as an inhibit or synchronous pacemaker, a reset input for the binary frequency multiplier (6) as well as, under certain conditions, for further circuit parts (3, 7) is present which, upon occurrence of spontaneous heart actions, sets the binary frequency multiplier as well as the other circuit parts which may, under certain conditions, be present to a preselected initial state.

6. A heart pacemaker according to claim 1, characterized by a changeover switch (11) for changing the binary frequency multiplier (6) over on its input side from output signals of the setting generator (5) to output signals for, for example, a test frequency of a test frequency generator (12, 13) for testing the battery condition (14).

* * * * *